United States Patent [19]

Nishioka et al.

[11] Patent Number: 4,529,267
[45] Date of Patent: Jul. 16, 1985

[54] ILLUMINATING SYSTEM FOR ENDOSCOPES

[75] Inventors: Kimihiko Nishioka; Hisao Yabe, both of Hachiouji, Japan

[73] Assignee: Olympus Optical Co., Ltd., Tokyo, Japan

[21] Appl. No.: 328,392

[22] Filed: Dec. 7, 1981

[30] Foreign Application Priority Data

Dec. 10, 1980 [JP] Japan ................................ 55-173200
Dec. 10, 1980 [JP] Japan ................................ 55-173201

[51] Int. Cl.³ ............................................... G02B 5/16
[52] U.S. Cl. ................................ 350/96.26; 350/96.25
[58] Field of Search ........................... 350/96.25, 96.26

[56] References Cited

U.S. PATENT DOCUMENTS

| | | | |
|---|---|---|---|
| 2,932,294 | 4/1960 | Fourestier et al. | 350/96.26 |
| 3,142,235 | 7/1964 | Siegmund | 350/96.25 |
| 3,166,395 | 1/1965 | Hicks | 350/96.25 |
| 4,279,247 | 7/1981 | Kinoshita | 350/96.26 |
| 4,281,929 | 8/1981 | Lord et al. | 350/96.26 |
| 4,390,012 | 6/1983 | Mizumoto | 350/96.26 |
| 4,403,273 | 9/1983 | Nishioka | 350/96.26 |

Primary Examiner—William L. Sikes
Assistant Examiner—Robert E. Wise
Attorney, Agent, or Firm—Cushman, Darby & Cushman

[57] ABSTRACT

An illuminating system for endoscopes comprising a light guide formed to be a flat surface or curved surface at the exit end and a concave lens or convex lens arranged in front of the exit end and made to be a totally reflecting surface on the peripheral surface so that all the illuminating light emitted out of the exit end of the light guide can be effectively utilized and the visual field of an observing system can be uniformly illuminated over a very wide range. A convex mirror or concave mirror is placed between the exit end of the light guide and a concave lens used also as a cover glass so as to adapt the illuminating system to a side view or perspective view type endoscope.

6 Claims, 21 Drawing Figures

INTENSITY OF ILLUMINATING LIGHT ON OBJECT SURFACE

ANGLE OF VIEW

ILLUMINATING SYSTEM FOR ENDOSCOPES

BACKGROUND OF THE INVENTION (a) Field of the Invention

This invention relates to endoscopes and more particularly to an illuminating system for endoscopes having an expanded illuminating range.

(b) Description of the Prior Art

In an endoscope, as the angle of view of the observing system becomes larger, an illuminating system which can illuminate a wider range is required. Recently, an endoscope having an observing system having an angle of view larger than 100 degrees has come to be used and, in response to it, the illuminating system which can illuminate a wider range has come to be required. There is known a conventional endoscope illuminating system which can illuminate a wide range and in which, as shown in FIG. 1, a concave lens 2 is arranged in front of a light guide 1. In the illuminating system having this arrangement, in order to make the range to be illuminated wider, the focal length may be made shorter by curving the concave surface of the concave lens 2 with a larger curvature but, if the concave lens 2 is so made, the brightness on the periphery of the visual field will become so lower than the brightness near the center of the visual field as to be impractical. Further, as shown in FIG. 1, the light coming out of the periphery of the light guide 1 will be refracted so greatly as to hit the peripheral surface $2a$ and chamfered portion $2b$ of the concave lens 2, will not contribute to the illumination and will be lost. FIG. 2 shows a relation between the angle of view and the intensity of the illuminating light reaching an object surface. The reason why the brightness on the periphery of the visual field is extremely lower than the brightness near the center of the visual field in the fact that, as shown in FIG. 3, when the ray (of the highest intensity among the rays coming out of the light guide 1) parallel with the fibers of the light guide is considered as a principal ray k, the concave lens 2 will have a strong distortion, that is to say, that the rate $d\omega/dh$ of the increase of the angle of refraction $\omega$ to the increase of the ray height h of the principal ray k will become quickly large with the increase of h. If considered with the Seidel aberration, the distortion will increase in proportion to the third power of h. Further, in order to avoid such loss of light as is described above, it is necessary to make the diameter of the concave lens 2 large enough. However, it will result in making the diameter of the endoscope large and is not desirable. In order to eliminate such defects, the peripheral surface $2a$ of the concave lens 2 may be made to be a reflecting surface. However, for that purpose, it is necessary to grind the peripheral surface $2a$ of the concave lens 2 and evaporatively deposit a metal film on it. However, there are defects that it is a trouble to grind the peripheral surface of the lens, it is difficult to evaporatively deposit a metal on the cylindrical surface and the cost becomes high.

SUMMARY OF THE INVENTION

A primary object of the present invention is to provide a small endoscope illuminating system wherein light emitted out of the periphery of the exit end face of a light guide can be also effectively utilized for illumination and the light amount on the periphery of the visual field is large and which can be made easily and cheaply.

According to the present invention, this object is attained by arranging an optical system having at least two curved surfaces (including the curved surface, too, in case it is made of the exit end face of the light guide) in the exit end part of the light guide and forming the optical system of at least one lens including a tubular reflecting means having a totally reflecting peripheral surface.

According to a preferred formation of the present invention, a single fiber is used as a tubular reflecting means and satisfies the following condition:

$$\sin \omega \leq \sqrt{n^2 - n_1^2}$$

wherein the reference symbol $\omega$ represents a half angle of view of the observing system and the reference symbols n and $n_1$ represent refractive indices respectively of the core and clad of the single fiber.

This and other objects of the present invention will become more apparent during the course of the following detailed description and appended claims.

DESCRIPTION OF THE PREFERRED EMBODIMENTS

Figure 4:
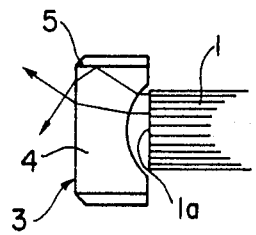
FIG. 4 is a formation view of an essential part, showing a first embodiment of the present invention.

FIG. 4 is of a first embodiment of the present invention in which a concave lens 3 formed of a single fiber is arranged in front (on the side of the object to be inspected) of the exit end face of a light guide 1. The reference numeral 4 denotes a core and 5 denotes a clad.

Figure 5:
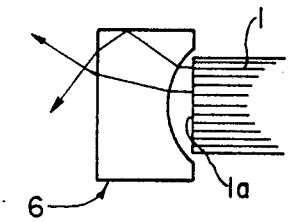
FIG. 5 is a formation view of an essential part, showing a second embodiment of the present invention.

The surface opposed to the exit end face 1a of the light guide of the single fiber provided thus with the clad 5 is ground to be concave to be made the concave lens 3. FIG. 5 is of another second embodiment in which the surface opposed to the exit end face 1a of the light guide 1 of a single fiber provided with no clad is ground to be concave to be made a lens 6.

By the way, such columnar concave lens made to eliminate the totally reflecting surface on the peripheral surface as a glass bar or plastic bar smooth on the peripheral surface or further a general concave lens ground to be a totally reflecting surface on the peripheral surface may be used besides the above mentioned embodiment in which the single fiber is ground to be the concave lens 3 or 6.

The concave lens using such single fiber, need not be ground on the peripheral surface or have a metal film evaporatively deposited on the peripheral surface and is therefore easy to make. Further, whereas, in the concave lens having a metal film evaporatively deposited on the peripheral surface, the reflecting rate is 90% at most, in the embodiment of the present invention in which the total reflection is utilized, the reflection factor is about 100%. The conventional type concave lens having a metal film evaporatively deposited on the peripheral surface has a potential problem that the metal film may be hurt during the assembling work but the embodiment of the present invention using a single fiber has no such fear.

Further, the concave lens 3 having the clad 5 shown in FIG. 4 is further preferable in the following points. That is to say:

(a) In a concave lens made by grinding the end surface of a single fiber having no clad to be concave as shown in FIG. 5 or by grinding the peripheral surface of a general concave lens to be a totally reflecting surface, if the peripheral surface is stained during the assembling, the total reflection will deteriorate and the reflection factor will be likely to reduce but, in a concave lens made by grinding the end surface of a single fiber provided with no clad to be concave, the reflection factor will not be reduced by the above mentioned cause.

(b) In the above mentioned concave lens 6 having no clad, as a binder is used on the peripheral surface in incorporating it, the reflection factor will reduce but, in the single fiber having the clad 5, the reflection factor will not be reduced by such case.

Figure 1:
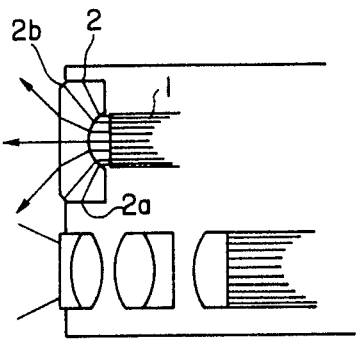
FIG. 1 is a view showing the formation of the tip part of a conventional endoscope.
Figure 2:
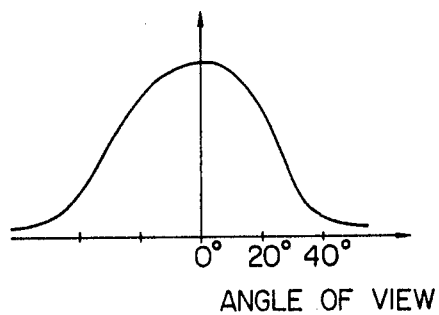
FIG. 2 is a diagram showing the variation of the illumination with the angle of view on a surface to be inspected by a conventional endoscope illuminating system.
Figure 3:
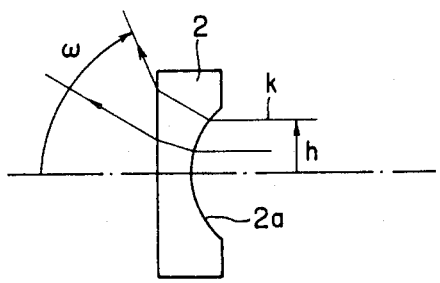
FIG. 3 is a view showing the refraction mode of a principal ray of a conventional endoscope illuminating system using a concave lens.
Figure 6:
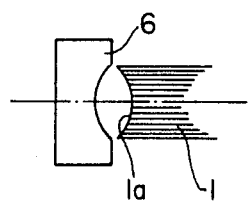
FIG. 6 is a formation view of an essential part, showing a third embodiment of the present invention.
Figure 7:
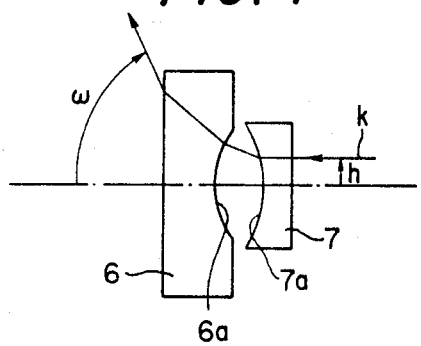
FIG. 7 is a view showing the refraction mode of a principal ray in an optical system in which the concave exit end face of the light guide in FIG. 6 is replaced with a lens.
Figure 8:
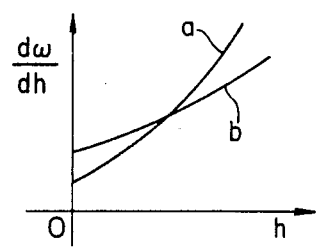
FIG. 8 is a diagram showing the variation of $d\omega/dh$ with the ray height h in the embodiment shown in FIG. 6 and a conventional illuminating system.
Figure 9:
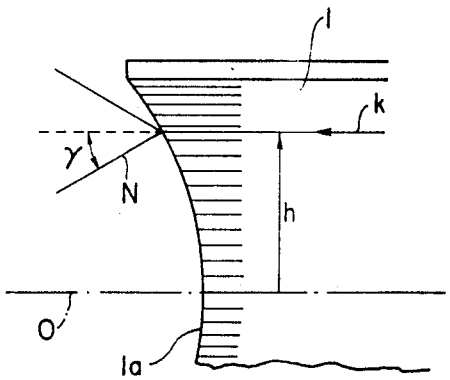
FIG. 9 is a view showing the refraction mode of a principal ray in case the end face of the light guide is a curved surface.

FIG. 6 shows a third embodiment of the present invention in which the exit end face 1a of the light guide 1 is made a concave and the same concave lens 6 as is shown in FIG. 5 is arranged in front of the concave end face 1. In FIG. 7, the exit end face 1a of the light guide 1 in the embodiment shown in FIG. 6 is replaced with a concave lens 7. The light emitted through the concave lens 6 out the light guide 1 in the embodiment shown in FIG. 6 just corresponds to a ray of light which enters parallelly on the optical axis of the concave lens 7 in FIG. 7 and passes through the concave lenses 7 and 6. Among the rays coming out of the respective fibers of the light guide 1, the ray of light parallel with the fibers is of the highest intensity among the rays coming out of the fibers. Therefore, if the angle ω after the refraction of the ray k parallel with the optical axis and incident upon the concave lens 7 in FIG. 7 is investigated, the expansion of the light will be able to be anticipated. In the lens system shown is FIG. 7, in order that the ray of an incident ray height h may be refracted by the angle ω, it will be gradually refracted by the two concaves 7a and 6a. Therefore, the value of the rate (dω/dh) of the increase of ω when the ray height h increases will not increase more rapidly with the increase of h than in the case that it is refracted by one concave surface 2a as in FIG. 3. That is to say, the distortion of the lens system shown in FIG. 7 is smaller than the distortion of the lens system consisting of one concave lens 2 shown in FIG. 3. Therefore, the lens system shown in FIG. 7, that is, the lens system of the embodiment of the present invention shown in FIG. 6 is better in the distribution of the light on the periphery of the visual field than the conventional lens system shown in FIG. 3. FIG. 8 is a diagram showing the relation between the ray height h and increasing rate (dω/dh). In this diagram, the curve a relates to the conventional system shown in FIG. 3 and the curve b relates to the embodiment of the present invention. As shown in this diagram, the formation according to the present invention is less in the increase of (dω/dh) with the increase of h and in the distortion than in the conventional example. In the third embodiment shown in FIG. 6, in case the exit end face 1a of the light guide 1 is curved with a larger curvature, the light coming out of the light guide 1 will be totally reflected by the end face 1a and will be lost. Therefore, there is a fixed limit to the angle of inclination of the exit end face 1a of the light guide 1. In FIG. 9, the ray k parallel with the axis O of the light guide 1 is considered. Generally, the ray k parallel with the light guide 1 is a ray of the highest intensity among the rays coming out of the height h and therefore, if this ray k is totally reflected on the end face 1a of the light guide, the light amount will be lost. If, as shown in FIG. 9, γ represents the angle of inclination (the angle made by the extension of the ray k and the normal N) of the exit end face 1a of the light guide 1 and the refractive index of the core of the light guide 1 is represented by n, the condition that the ray k makes no total reflection will be given by the following condition (1):

$$|\sin \gamma| \leq (1/n) \qquad (1)$$

In fact, the value of γ will be allowed until the range shown by the condition (2):

$$|\sin \gamma| \leq (2/n) \qquad (2).$$

Figure 10:
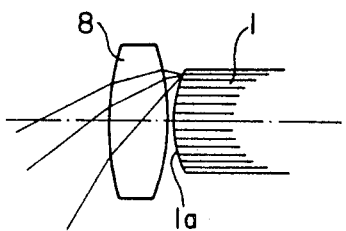
FIG. 10 is a formation view of an essential part, showing a fourth embodiment of the present invention.

FIG. 10 shows a fourth embodiment in which the exit end face 1a of the light guide 1 is made a convex and a convex lens 8 is arranged in front of the light guide 1. In this embodiment, the principal rays coming out of respective fibers of the light guide 1 are once condensed by the convex 1a of the light guide 1 and convex lens 8 and then expand to illuminate a wide range. The rays are gradually refracted by so many faces that the distortion will become small and a favorable distribution of the rays will be obtained. By the way, the above described conditions (1) and (2) can be applied as they are to the conditions relating to the angle of inclination of the exit end face 1a of the light guide 1. In this embodiment, the wider the angle, the much shorter the focal length of the convex lens 8 and the image of the exit end face 1a of the light guide 1 may be formed. Therefore, it is not adapted to a superwide angle.

Figure 11:
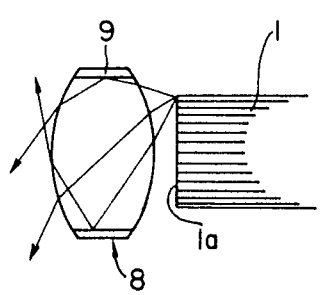
FIG. 11 is a formation view of an essential part, showing a fifth embodiment of the present invention.

FIG. 11 shows a fifth embodiment which is different from any of the above mentioned embodiments in respect that the exit end face 1a of the light guide is flat and a clad 9 is provided on the peripheral surface of the convex lens 8. In this embodiment, the rays emitted out of the light guide 1 are once condensed and then expand to illuminate a wide range. As the peripheral surface of the convex lens 8 is a totally reflecting surface, the light amount will not be lost and a wider range can be illuminated. In this embodiment, too, it is more preferable to form the exit end face 1a of the light guide 1 to be convex and the convex lens 8 may be replaced with a general convex lens made a totally reflecting surface on the peripheral surface or a convex lens made by grinding a single fiber.

Now, in relation to the embodiment in which a clad is provided and a single fiber is used, the conditions for obtaining an illuminating light which can cover the range of the predetermined angle of view of the observing system of an endoscope shall be explained in the following.

Figure 12:
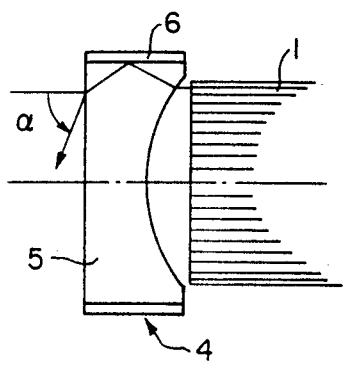
FIG. 12 is a view for explaining the relation between the refraction of the ray and the refractive index of the single fiber in the embodiment shown in FIG. 4.

When the angle of view of the observing system of the endoscope is $2\omega$, in order that an illuminating light may reach the entire visual field of the observing system, it will be necessary that the value twice as large as the angle $\alpha$ shown in FIG. 12 should be larger than $2\omega$. If the refractive index of the single fiber core is n and the refractive index of the clad is $n_1$, $$\sin \alpha = \sqrt{n^2 - n_1^2} . \tag{3}$$

Therefore, it is necessary that n and $n_1$ should satisfy the following formula:

$$\sin \omega \leq \sqrt{n^2 - n_1^2} . \tag{4}$$

For example, in case $2\omega = 120$ degrees, if $n = 1.76$ and $n_1 = 1.52$, the formula (4) will be satisfied.

Figure 13:
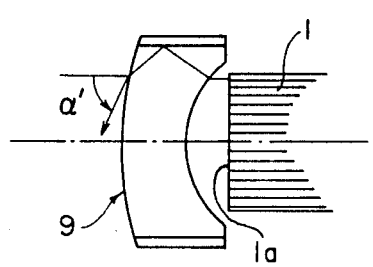
FIGS. 13 through 21 are formation views of essential parts, showing respectively other embodiments of the present invention.

FIG. 13 is of a sixth embodiment using a concave lens 9 made of a single fiber and having the convex surface on the object side. In this embodiment, in case a light comes out of the lens 9, it will be refracted so much more strongly that the condition shown by the formula (4) will be loosened and such values of n and $n_1$ as satisfy the following formula may be selected:

$$\tfrac{1}{2} \sin \omega \leq \sqrt{n^2 - n_1^2} .$$

Figure 14:
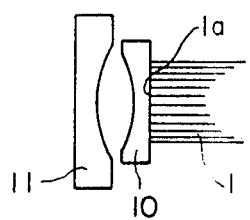

FIG. 14 is of a seventh embodiment in which two concave lenses 10 and 11 are arranged in front of the light guide 1 and the flat face side of the concave lens 10 is cemented to the exit end face 1a of the light guide 1. That is to say, the lens system shown in FIG. 7 is arranged on the end face 1a of the light guide 1. Therefore, its action is the same as that of the third embodiment shown in FIG. 6.

Figure 15:
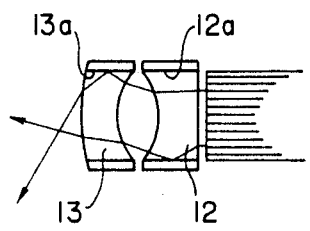

FIG. 15 is of an eighth embodiment in which single fibers 12 and 13 each ground to be concave on one surface are used instead of the concave lenses 10 and 11 in the seventh embodiment shown in FIG. 14. It is needless to say that, the same as in this embodiment, a single fiber ground to be concave on one face may be used instead of the concave lens 6 shown in FIG. 6. In the case of these embodiments, as shown in the drawing, the light hitting the peripheral surfaces 12a and 13a of the lenses 12 and 13 of the single fibers will be totally reflected, therefore the loss of the light amount will be small and the outside diameters of these lenses will be able to be made small. By the way, these single fibers may have no clad. Further, a lens made by grinding the end face of a glass bar smooth on the peripheral surface so as to be a curved surface may be used instead of the single fiber. Further, with a general lens ground on the peripheral surface or having a reflecting film evaporatively deposited on the peripheral surface as in the embodiment shown in FIG. 6 and others, the same effect as of the lens using the above described single fiber is obtained.

Figure 16:
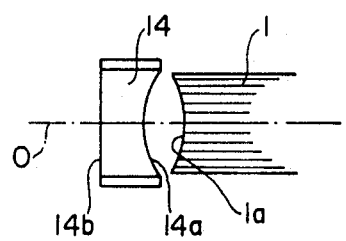
Figure 17:
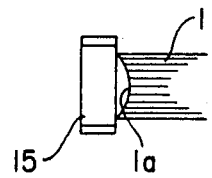

FIG. 16 is of a ninth embodiment in which a lens 14 having a curved surface formed by working a heterogeneous medium is arranged in front of the light guide 1 having the exit end face 1a made a concave. In this embodiment, the refractive index of the lens 14 may vary so that the distortion may be removed, that is to say, the light may be gradually refracted by the concave 14a and the variation of the refractive index of the lens 14. For example, in the case of the embodiment shown in FIG. 16, such heterogeneous medium as reduces the refractive index as the optical axis O is separated may be used for the lens 14. Further, there may be used such heterogeneous medium with which the refractive index varies in the direction along the optical axis O, in the lowest on the concave 14a side, is gradually higher toward the flat face 14b and is highest on the flat face 14b side. Also, as shown in FIG. 17, a lens 15 made of a heterogeneous medium flat on both faces may be arranged in front of the light guide 1 concave on the exit end face. Also, in the case of the embodiment using a lens made of such heterogeneous medium, a clad may be provided on the peripheral surface of the lens so that the loss of the light amount may be prevented.

Figure 18:
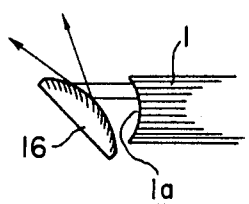

FIG. 18 shows a tenth embodiment in which a convex reflecting mirror 16 is arranged in front of the light guide 1 having a concave exit end face 1a so that an illuminating system which is excellent in the distribution of light and which can illuminate a very wide range can be made.

Figure 19:
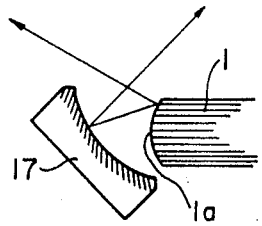

FIG. 19 shows an eleventh embodiment in which a concave reflecting mirror 17 is arranged in front of the light guide 1 having a convex exit end face 1a. It is convenient to use the embodiment shown in FIG. 18 or 19 as combined with a side view or perspective view type endoscope. In the same manner, a convex reflecting mirror inclined to the optical axis may be used instead of the concave lens 11 in the seventh embodiment shown in FIG. 14. According to such embodiment in which the concave reflecting mirror inclined to the optical axis is arranged in front of the light guide 1 curved on the exit end face 1a or the lens and curved reflecting mirror are combined with each other and are arranged in front of the light guide 1 flat on the exit end face, there is obtained a side view or perspective view illuminating system which can be provided also with both a function of bending the light path for the side view or perspective view and a function of correcting aberrations (a function of brightly and well illuminating even the periphery of the visual field), is simple in formation and is favorable in the distribution of light.

Figure 20:
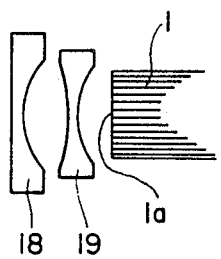

Further, FIG. 20 is of a twelfth embodiment in which two concave lenses 18 and 19 are arranged in front of the exit end face 1a of the light guide 1 and one of them is made a lens concave on both sides so that the refracting action can be more gradually performed on each curved surface and therefore an illuminating system lower in distortion may be obtained.

Figure 21:
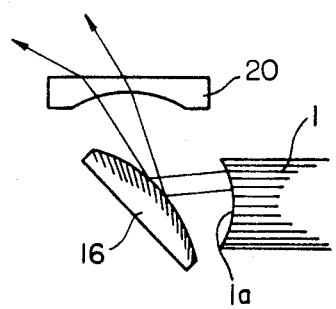

FIG. 21 is of a thirteenth embodiment in which a concave lens 20 which is also a cover glass is arranged in front of the reflecting mirror 16 in the tenth embodiment so that a better illuminating system may be made.

We claim:

1. An illuminating system for endoscopes comprising a light guide having an exit end face which is either of a flat surface and curved surface, and an optical system comprising at least one lens formed of a single fiber comprising a core and clad, the lens disposed in front of an end face of the light guide; and a totally reflecting surface disposed about the lens or lenses and wherein said single fiber satisfies the following conditions:

$$\sin \omega \leq \sqrt{n^2 - n_1^2}$$

wherein the reference symbol $\omega$ represents a half angle of view of an observing system of endoscopes and the reference symbols $n$ and $n_1$ represent refractive indices respectively of said core and clad of said single fiber.

2. An illuminating system for endoscopes according to claim 1 wherein said lens further has at least one curved surface.

3. An illuminating system for endoscopes according to claim 1 wherein said exit end face of said light guide is curved.

4. An illuminating system for endoscopes according to claim 1 wherein said exit end face is a flat surface, and said optical system is arranged in front of and adjacent to said exit end face of said light guide and has at least one curved surface.

5. An illuminating system for endoscopes according to claim 1 wherein said exit end face is a curved surface, and said optical system is arranged in front of and adjacent to said exit end face of said light guide and has at least one curved surface.

6. An illuminating system for endoscopes according to claim 1 wherein said reflecting surface is tubular in shape.

* * * * *